(12) United States Patent
Kappel et al.

(10) Patent No.: US 11,857,214 B2
(45) Date of Patent: Jan. 2, 2024

(54) MULTI-FUNCTIONAL MEDICAL DEVICE AND RELATED

(71) Applicant: Boston Scientific Scimed, Inc., Maple Grove, MN (US)

(72) Inventors: Gary Kappel, Acton, MA (US); Sean Fleury, Brighton, MA (US); Paul Smith, Smithfield, RI (US); Brandon Zalewski, Clinton, MA (US); Laurie Soderbom, Nashua, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 234 days.

(21) Appl. No.: 17/139,175

(22) Filed: Dec. 31, 2020

(65) Prior Publication Data
US 2021/0121190 A1 Apr. 29, 2021

Related U.S. Application Data

(63) Continuation of application No. 15/650,186, filed on Jul. 17, 2017, now Pat. No. 10,905,451, which is a (Continued)

(51) Int. Cl.
| | |
|---|---|
| *A61B 17/295* | (2006.01) |
| *A61B 17/29* | (2006.01) |
| *A61B 18/14* | (2006.01) |
| *A61B 18/08* | (2006.01) |
| *A61B 90/00* | (2016.01) |
| *A61B 17/32* | (2006.01) |

(Continued)

(52) U.S. Cl.
CPC ............ *A61B 17/295* (2013.01); *A61B 17/29* (2013.01); *A61B 18/1445* (2013.01); *A61B 17/068* (2013.01); *A61B 17/34* (2013.01); *A61B 18/085* (2013.01); *A61B 2017/2901* (2013.01); *A61B 2017/2926* (2013.01); *A61B 2017/320044* (2013.01); *A61B 2018/00595* (2013.01); *A61B 2018/1455* (2013.01); *A61B 2090/0817* (2016.02); *A61B 2217/005* (2013.01); *A61B 2217/007* (2013.01); *A61B 2218/002* (2013.01); *A61B 2218/007* (2013.01)

(58) Field of Classification Search
None
See application file for complete search history.

(56) References Cited

U.S. PATENT DOCUMENTS

| | | |
|---|---|---|
| 5,170,925 A | 12/1992 | Madden |
| 5,391,166 A | 2/1995 | Eggers |

(Continued)

*Primary Examiner* — Michael W Kahelin
(74) *Attorney, Agent, or Firm* — Bookoff McAndrews, PLLC

(57) ABSTRACT

A medical device including an elongate member having a proximal end, a distal end, and a lumen extending therebetween. The medical device may further include an end-effector disposed at the distal end of the elongate member. The end-effector may include a plurality of arms pivotally connected to one another, wherein each arm includes a tissue-contacting surface, a first portion of the tissue-contacting surface including a plurality of ridges configured to grasp tissue. Further, the tissue-contacting surface may include a channel oriented substantially parallel to a longitudinal axis of the medical device.

8 Claims, 5 Drawing Sheets

Related U.S. Application Data continuation of application No. 15/090,741, filed on Apr. 5, 2016, now Pat. No. 9,737,321, which is a continuation of application No. 14/661,588, filed on Mar. 18, 2015, now Pat. No. 9,333,003, which is a continuation of application No. 13/755,579, filed on Jan. 31, 2013, now Pat. No. 9,011,434.

(60) Provisional application No. 61/592,764, filed on Jan. 31, 2012.

(51) Int. Cl.
*A61B 17/068* (2006.01)
*A61B 17/34* (2006.01)
*A61B 18/00* (2006.01)

(56) References Cited

U.S. PATENT DOCUMENTS

| | | | |
|---|---|---|---|
| 5,452,837 A * | 9/1995 | Williamson, IV | ............ A61B 17/07207 227/176.1 |
| 5,476,479 A * | 12/1995 | Green | ........ A61B 17/2909 606/205 |
| 5,728,112 A | 3/1998 | Yoon | |
| 5,797,927 A | 8/1998 | Yoon | |
| 5,819,738 A | 10/1998 | Slater | |
| 6,099,550 A | 8/2000 | Yoon | |
| 6,139,508 A | 10/2000 | Simpson et al. | |
| 7,131,978 B2 | 11/2006 | Sancoff et al. | |
| 2003/0065358 A1 * | 4/2003 | Frecker | ........... A61B 17/29 606/205 |
| 2004/0044363 A1 * | 3/2004 | Fowler | ........... A61B 17/1285 606/205 |
| 2004/0172057 A1 | 9/2004 | Guillebon et al. | |
| 2005/0101952 A1 * | 5/2005 | Lands | ........... A61B 18/1445 606/51 |
| 2005/0245841 A1 | 11/2005 | Turturro et al. | |
| 2006/0079874 A1 | 4/2006 | Faller et al. | |
| 2008/0015566 A1 | 1/2008 | Livneh | |
| 2008/0262539 A1 | 10/2008 | Ewers et al. | |
| 2009/0209991 A1 | 8/2009 | Hinchcliffe et al. | |
| 2010/0179545 A1 | 7/2010 | Twomey | |
| 2011/0270280 A1 | 11/2011 | Saliman | |
| 2012/0116391 A1 | 5/2012 | Houser et al. | |
| 2013/0267786 A1 | 10/2013 | Vayser et al. | |

* cited by examiner

MULTI-FUNCTIONAL MEDICAL DEVICE AND RELATED

RELATED APPLICATION(S)

This application is a continuation of U.S. patent application Ser. No. 15/650,186, filed on Jul. 17, 2017, which is a continuation of U.S. application Ser. No. 15/090,741, filed on Apr. 5, 2016, now U.S. Pat. No. 9,737,321, which is a continuation of U.S. application Ser. No. 14/661,588, filed on Mar. 18, 2015, now U.S. Pat. No. 9,333,003, which is a continuation of U.S. application Ser. No. 13/755,579, filed on Jan. 31, 2013, now U.S. Pat. No. 9,011,434, which claims the benefit of priority of U.S. Provisional Application No. 61/592,764, filed on Jan. 31, 2012, each of which is incorporated herein by reference in its entirety.

FIELD OF THE INVENTION

Embodiments of this disclosure relate generally to medical devices and procedures. In particular, embodiments of the present disclosure relate to minimally invasive medical devices and procedures for manipulating tissues from inside a patient's body.

BACKGROUND OF THE INVENTION

An endoscopic procedure typically involves indirect observation of a surgical field through an endoscope or similar device inserted through an incision or a natural anatomical opening. The endoscope generally takes the form of a long, flexible tube, including a light conductor along with one or more channels for inserting medical devices. Endoscopes provide platforms for employing numerous tools as end-effectors, such as devices to grasp, clip, sever, and remove objects from inside the body.

During surgical procedures, the need for precision end-effectors is critical to ensure safe, effective, quick, and successful outcomes. Additionally, the time and effort required to exchange the required end-effectors during surgery could also be a critical factor during a procedure. Multiple functionalities provided by a single end-effector may reduce the use of multiple devices thereby reducing the invasiveness of the procedure. Thus, it would be desirable to use end-effectors with multiple capabilities.

SUMMARY OF THE INVENTION

Embodiments of this disclosure relate generally to medical devices and procedures. In particular, embodiments of the present disclosure relate to minimally-invasive medical devices and procedures for manipulating tissues from inside a patient's body.

In one embodiment, a medical device may include an elongate member having a proximal end, a distal end, and one or more lumens (for additional functionality) extending therebetween. The medical device may also include an end-effector disposed at the distal end of the elongate member, the end-effector may include plurality of arms, jaws, or other components pivotally connected to one another. In addition, each arm may include one or more tissue-contacting surfaces, a first portion of a tissue-contacting surface including a plurality of ridges configured to grasp and retain tissue. Further, the tissue-contacting surface may include a channel oriented substantially parallel to a longitudinal axis of the medical device.

In various embodiments, the medical device may include one or more of the following additional features: only one of a plurality of arms may be configured to move; the entire tissue-contacting surface may include ridges; a second portion of the tissue-contacting surface may include a mating surface having one or more teeth or ridges; a channel may extend in a direction that is substantially parallel to a longitudinal axis of the elongate member; a device may further comprise one or more cutting elements configured to be advanced through the channel; a cutting element may be a cautery device; a suction and/or irrigation lumen; the medical device may further comprise one or more locking devices or mechanisms for selectively fixing a position of at least one of the plurality of arms; and a distalmost surface of at least one of the plurality of arms includes an atraumatic surface.

In another embodiment, a medical device may include an elongated member having a proximal end, a distal end, and a lumen or shaft extending therebetween. The medical device may also include a control member extending within a lumen of the elongated member, wherein the control member includes a distal end and a proximal end. The medical device may also include an end-effector disposed at a distal end of the control member, and the end-effector may include at least two arms connected at its proximal end to form a jaw-like structure, wherein each of the arms includes a tissue-contacting-surface. The medical device may further include a plurality of retractable projections disposed on at least one of the tissue-contacting surfaces.

In various embodiments, a medical device may include one or more of the following additional features: only one of a plurality of arms may be configured to move; the medical device may further include one or more locking devices for selectively fixing a position of at least one of the plurality of arms; the projections may be configured to selectively retract into respective openings on at least one of the tissue-contacting surfaces; both tissue-contacting surfaces may include a plurality of retractable projections; and at least one of the arms may further include a substantially flat surface disposed proximate the tissue-contacting surface.

Further, in another embodiment, a medical device may include an elongated member having a proximal end, a distal end, and a lumen extending therebetween. The medical device may also include a control member extending within the lumen of the elongated member, the control member having a distal end and a proximal end. In addition, the medical device may include an end-effector disposed at a distal end of the control member, the end-effector including at least two arms connected at its proximal end to form a jaw-like structure, wherein each of the arms includes a substantially flat inner surface disposed adjacent to a plurality of ridges.

In various embodiments, the medical device may include one or more of the following additional features: only one of a plurality of arms may be configured to move; the medical device may further include a locking device for selectively fixing a position of at least one of the plurality of arms; at least one of the plurality of ridges further includes at least one selectively deployable projection; and the substantially flat inner surface may include a plurality of substantially flat inner surfaces Additional objects and advantages of the present disclosure will be set forth in part in the description, which follows, and in part will be obvious from the description, or may be learned by practice of the present disclosure. The objects and advantages of the present disclosure will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the disclosure and together with the description, serve to explain the principles of the disclosure. Wherever possible, the same reference numbers will be used throughout the drawings to refer to the same or like parts.

DESCRIPTION OF THE EMBODIMENTS

Reference will now be made in detail to embodiments of the disclosure, an example of which is illustrated in the accompanying drawings. For convenience, the term "tissue grasper" will be used throughout this application.

Overview

The present disclosure provides a tissue grasper including two arms forming a jaw-like structure. The tissue grasper may be an end-effector for holding tissue and other target objects. The arms of the end-effector may be rotatably connected to one another to permit the arms to move between an open and closed configuration. A proximal portion of one or both arms may be operable connected to a control member. The control member extends through an elongated member extending between the end-effector at its distal end to an end-effector actuator means (hereafter, controller) present at its proximal end. Articulating the controller actuates the end-effector to effectuate opening and closing of the arms. The two arms may be differentiated as an "upper" and "lower" jaw. Various configurations of end-effector actuation, structure, and functions are described in the embodiments of the disclosure. Further, as used in this disclosure, "distal" refers to a position or direction further from the user, and "proximal" refers to a position or direction opposite "distal" and closer to the user.

More particularly, the present disclosure provides a tissue-grasping device for securely holding and manipulating tissues. Manipulation includes, but is not limited to, cutting, sectioning, stapling, clamping, cauterizing, grasping, holding, or scraping of tissue. Clamping as used in this disclosure means holding, grasping, and/or fastening tissues together. The various methods of manipulation are described in detail hereafter.

Exemplary Embodiments

Figure 1A:
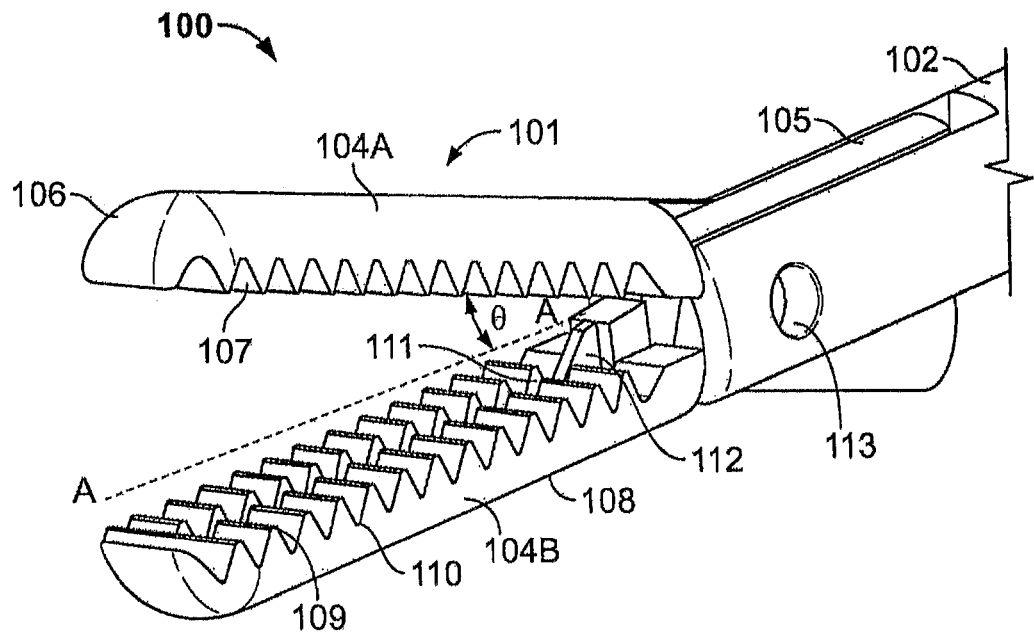
FIGS. 1A-1D illustrate perspective views of a tissue grasper in an open configuration, according to some embodiments of the present disclosure.

FIG. 1A depicts a tissue grasper 100 in an open configuration according to an embodiment of the present disclosure.

The tissue grasper 100 includes an end-effector 101 extending distally from an elongated member 102. A control member (not shown) extends through the elongated member 102 translating the movements from a controller or handle (not shown) present at the proximal end of the elongated member 102. The elongate member 102 includes a clevis member 103 that is present at its distal end.

The end-effector 101 includes two jaws or arms, an upper arm 104A and a lower arm 104B, (hereafter, arms 104) pivotally connected to each other. The jaws may be pivotably coupled to the clevis 103, for example, via a pivot pin 113. A proximal end 105 of arms 104 may be rotatably connected to one another to permit arms 104 to move between them. A control member (not shown) may be operably connected to the proximal end 105 of one or both of arms 104, so that actuating the arms 104 at their proximal end 105 translates into movement of the arms 104 at their distal end 106. While both arms 104 may be pivotable relative to one another, in some embodiments, one of the arms 104 may be fixed, and the other arm 104 may be movable, so the control member actuates only the movable arm 104.

The cross section of the arms 104 may also vary on their proximal and distal ends 105, 106. The distal end 106 of the arms 104 includes an inner surface 107, and an outer surface 108. As shown in FIG. 1, inner surface 107 is a tooth-type or ridge-like mating surface, thereby forming a substantial tissue contacting area to increase gripping and friction applied to the tissue, to reduce the likelihood of the grasped tissue from slipping. In some embodiments, the tissue contacting area may be substantially flat. At their distal ends 106, arms 104 may be linear, as shown in FIG. 1, but in alternate embodiments, the arms 104 may also be curved. In some embodiments, inner surface 107 may include surface roughening to enhance friction for improved tissue grasping. In addition, any suitable surface of arms 104 may include any desired surface roughening.

Figure 1B:
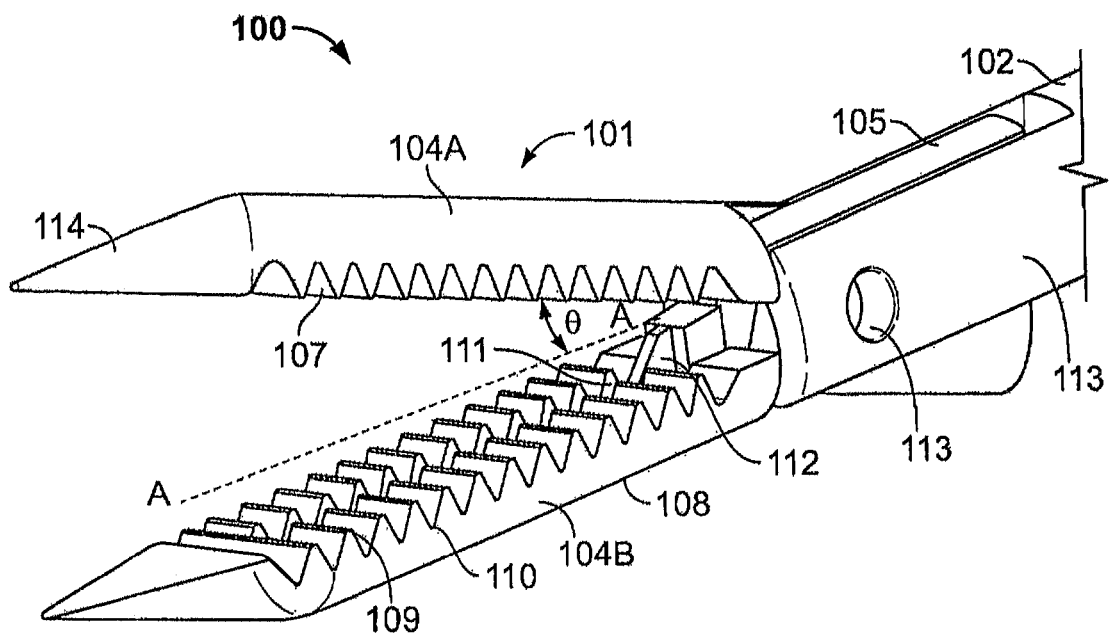
Figure 1C:
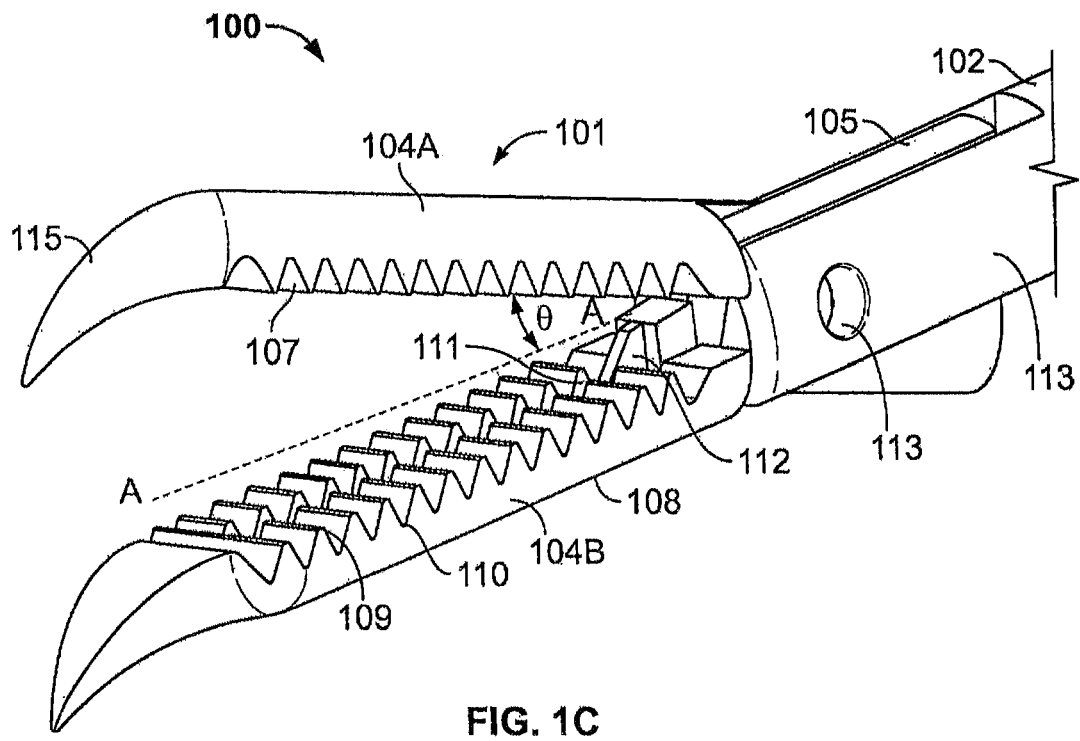
Figure 1D:
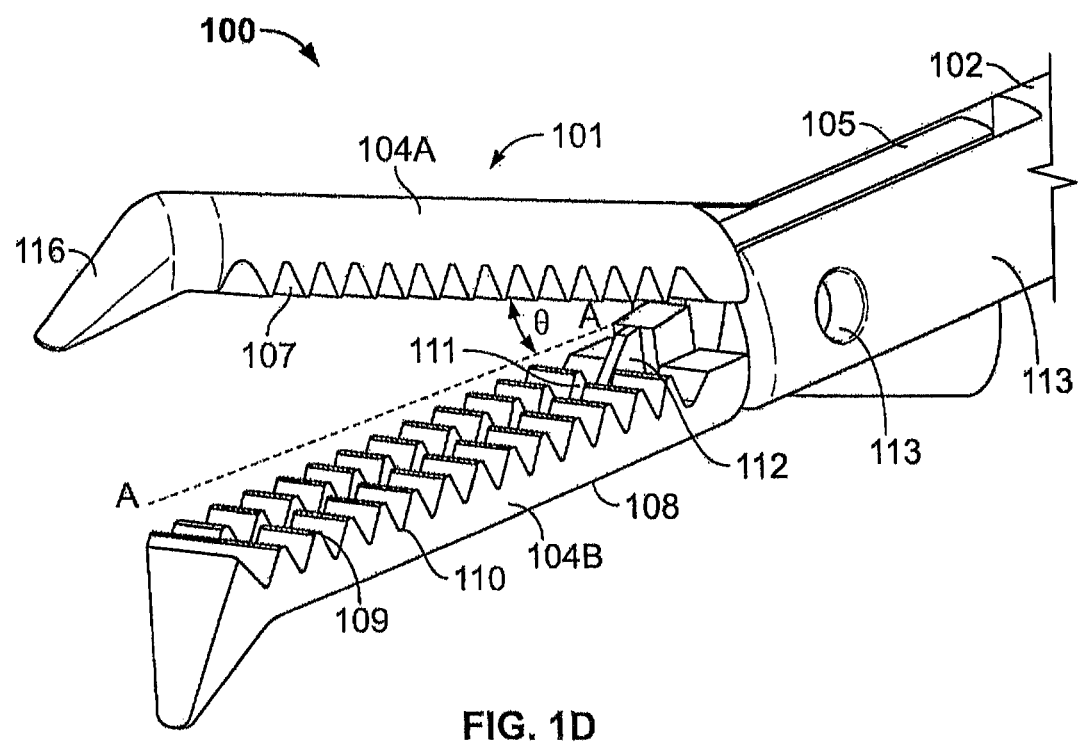

In additional embodiments, as shown in FIGS. 1B-1D the distal end 106 of the upper arm 104A may be varied in shapes and sizes. FIG. 1B depicts a spear headed tip 114, which may be used in skewering obstructing or unwanted tissues. The sharp end may also be used to tear open tissues to reach otherwise inaccessible areas within the body. The distal end 106 may also be shaped as a curved beak 115 like structure as depicted in FIG. 1C. Alternatively, the distal end may be tapered laterally giving rise to a flattened edge 116 as shown in FIG. 1D. The flattened edge 116 may also be beveled to prevent injury to the tissue. The modified distal ends 114, 115 and 116 may also be used for scraping plaque or debris adhered to the tissue. The modified distal ends 114, 115, 116 may also be used as a wedge to separate tissue layers or to single out vascular structures from a bundle. The distal end modifications may be present on the lower arm 104B or on both the arms 104. In some embodiments, spear headed tip 114 may include a flat, elongated edge that may aid in scraping or cutting. For example, rather than tip 114, a distalmost end of one or more of arms 104 may be formed as a flat edge.

The inner surfaces 107 of the arms 104 comprise ridges 109 and grooves 110 of suitable dimension. The cross section of the ridges 109 may be an angular slope, such as "V" shaped ridges 109. Alternatively, in other embodiments, the cross section of the ridges 109 may be rectangular, semicircular, or a combination of shapes. The ridges 109 may also lie parallel to one another on any axis in a lateral plane. Additionally, the ridges 109 may also be intersecting each other. The grooves 110 may also intersect with one another at any desired angle. Further, the ridges 109 may be present on at least one of the distal ends 106 of the arms 104. Alternatively, the ridges 109 may be present on both arms 104, seated within grooves 110 on the ridges 109. The ridges may vary in shape or dimension, and the inner surfaces 107 may provide corresponding grooves 110 to accommodate the ridges 109. Further, ridges 109 may have different heights, widths, and lengths.

The inner surface 107 on at least one of the arms 104 may also include bisection along the length of the arm 104. The bisection may take the form of a channel 111, allowing an element such as a blade to advance to the distal end 106. The channel 111 may also be present on both the inner surfaces 107, and may be of similar or different dimensions. The lumen and channel may consist of an opening for passage of exemplary tools through the device by the user. Such exemplary tools may include, but are not limited to, one or more needles, blades, or cautery tools. The channel may run parallel to the longitudinal axis, may be present at an angle, or may have a curve or bend.

The embodiment shown in FIGS. 1A-D also includes an advancing member, such as a cautery blade in the form of a cutter tool 112. In addition, the cutter tool 112 may be any other cautery tool, such as an electrocautery blade, a coagulation forceps, suction cautery devices, laparoscopic electrodes, laser fibers, lithotripters, and electrode cautery tips, which may include ball-tip, needle, and extended or flat blade electrodes. Further, the embodiments of FIGS. 1A-D may include any suitable suction and/or irrigation device. In some embodiments, the advancing member may include one or more channels, having a desired configuration, running at least partially along the length of the advancing member. For example, the channel may run parallel to the advancing member. Alternatively, the channel may be angled or curved with respect to the advancing member.

As shown in FIG. 1B, the cutter tool 112 may be a cautery blade, which is present at the proximal side of the distal end of the arm. The cutter tool 112 may be connected to a control member (not shown), and may be actuated by articulating the controller present at the proximal end of the control member. If connecting cutter tool 112 to the existing controller proves inconvenient, then an additional control member may be provided. The cutter tool 112 may be advanced or retracted along the length of the inner surface 107, with the dimensions of the tool being accommodated within the channel 111 bisecting the inner surface 107.

Tissue or vessel excision may lead to blood loss and further complications during surgery. The tissue grasper 100 with the integrated cutter tool 112 may allow for cauterizing tissue present within the arms 104 of the tissue grasper 100, thereby preventing slippage of the ends of the cut tissue. This may especially be useful in the case of blood vessels and ducts. In some embodiments, a cautery tool (e.g., an electrocautery blade) may be able to operate cold for cutting. That is, energy may not be required for cutting of tissue. However, in some cases, energy may be applied either to improve cutting or to contain bleeding through cauterization of tissue.

The cutter tool 112 may be replaced by a suction tool in some embodiments. The suction tool may be shaped similar to a Touhy needle, which can penetrate the grasped tissue and drain the fluids trapped within it. The suction tool may be in turn connected to a vacuum pump. In addition, the cutter tool 112 may be replaced by an irrigation tool for connection to an irrigation pump. The irrigation tool may be used to flush, e.g., tissue or other bodily matter from the treatment site.

The tissue grasper 100 may also integrate a tissue stapling or fastening means (not shown). Tissue stapling comprises a stapling element that may be disposed on at least one of inner surfaces 107. In another embodiment (not shown), two interlocking pieces of a stapling means are disposed on the two inner surfaces 107. When tissue is grasped between the open arms 104, the staple may be inserted and secured in place by the force provided during the closure of the arms 104. The stapling driving and forming operation could also be achieved by the advancing forward, i.e., proximal to distal, or by pulling rearward, i.e., distal to proximal, of a staple driving mechanism.

The tissue grasper 100 may also include a clamping element (not shown), which may be a "U" shaped elongate structure whose ends may be compressed towards one another and locked to form a fastening or sealing structure. In one embodiment, a clamp may be disposed between the distal ends 106 of the arms 104, wherein the clamp ends are towards the distal end 106. When tissue is grasped between the open arms 104, the clamp may be tightened and the ends secured in place by the force provided during the closure of the arms 104. Further modifications to the inner surface 107 are hereafter provided in the additional embodiments of this disclosure.

The outer surface 108 of the distal end 106 may be of any suitable shape that provides an atraumatic surface, such as beveled edges and rounded corners, to soft tissue. If desired, the end-effector 101 can be completely retracted into a protective sheath (not shown), and in one embodiment, the end-effector 101 can be completely withdrawn into an endoscope or similar instrument (not shown). The retracted configuration could prove useful for moving the unit through a patient's body lumens in preparation for use.

As described above, cauterization features may be incorporated by use of an electrocautery blade. In this embodiment, the inner surface 107 is formed of insulated or non-conductive material, for example, ceramic, plastic or any other suitable material known in the art. In other embodiments, the outer surface 108 may be made of any rigid material, such as metals, plastics, ceramics, or any other suitable material, which is biocompatible, and atraumatic to tissues. The outer surface 108 may also be coated with radio opaque materials, such as metals. Alternatively, the plastic or ceramic components may be ingrained with metal particulates to improve radio visibility. Power may be supplied to the electrocautery blade through an additional channel (not shown) provided in elongated member 102.

As best seen in FIG. 1, the inner surface 107 is oriented at an angle relative to the axis A-A' of the elongated member 102. In this embodiment, the inner surface 107 is at an angle $\theta$, however, in other embodiments, angle $\theta$ may be more or less than 90 degrees. Further, although angle $\theta$ is substantially the same in each arm 104, it should be appreciated that angle $\theta$ may be the same or different for one or more arms 104. Inner surface 107 engages and grasps the tissue segments that are retained within the space between arms 104. To enhance the grasping of the tissue segments within the space, angle $\theta$ may be less than or equal to 90 degrees.

In additional embodiments, the distal end 106 of the upper arm 104A may include a curved end. The end may be tapering in all directions leading to a spear headed tip 114 as shown in FIG. 1B. The spear headed tip 114 may be useful in skewering obstructing tissues. The spear headed tip 114 may also be curved to form a beak like structure as shown in FIG. 1C. Alternatively, the distal end 106 may be tapered laterally giving rise to a flattened edge 116 as shown in FIG. 1D. The edge may also be blunt and beveled to prevent injury to the tissue. The modified distal ends 114, 115, 116 may also be used for scraping plaque or debris adhered to the tissue. The flattened edge 116 may also be used as a wedge to separate tissue layers or to single out vascular structures from a bundle. Any component or the instrument as a whole may include a bipolar construction having areas of opposite polarity with insulation between components.

Figure 2:
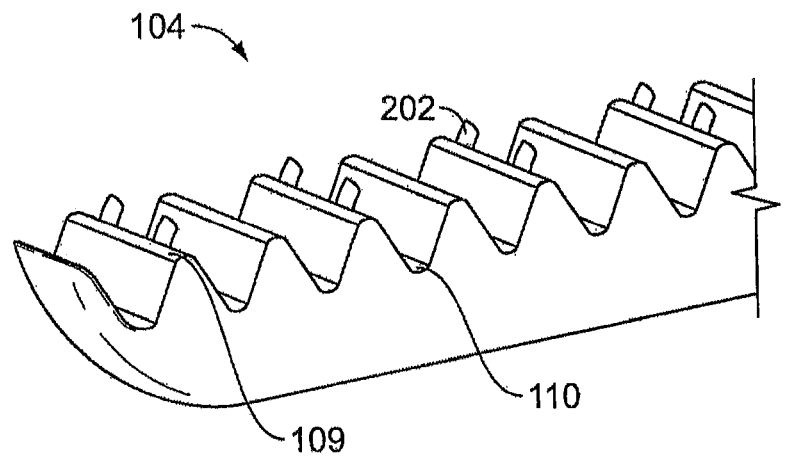
FIG. 2 illustrates an arm of a tissue grasper, according to an embodiment of the present disclosure.

In another embodiment, as shown in FIG. 2, the inner surface 107 of the end-effector 101 may also include barb-like elements that can be advanced or retracted. The barbed elements (hereafter, projections 202) may penetrate the tissue, to provide a better grip on slippery or dense tissue.

The projections 202, formed as rigid protrusions or extensions, are disposed on at least one of the inner surfaces 107. Alternatively, the projections 202 may be made of flexible material, and may have hooked ends to grab on to tissue. The projections 202 may also be an actuable element that can be advanced (from below flush with inner surface 107) to the desired length for the required tissue engagement, retracted, or held in position. The projections 202 may also be tubular structures, such as a Touhy needle like structure. The lumen on the tubular structure may be connected to a drainage system or a vacuum suction to drain fluids from grasped tissue. The tubular structures may also inject antiseptic formulations or anesthetics to prevent sepsis and relieve pain.

The inner surface 107, as shown in FIG. 2, also includes ridges 109 and grooves 110, as explained in connection with the first embodiment. The projections 202 may be advanced through slots (not shown) on the inner surface 107. The projections 202 may be connected to a controller via suitable control members (not shown). In some embodiments, the projections 202 may be actuated with a wedge-like deployment means within the end-effector, wherein distal movement of wedge pushes the projections up. In case the inner surface 107 is ridged, the slots may also be present on the ridges 109 or in the grooves 110. In addition, the tissue grasper 100 as described in this embodiment, may also include the variations described above in connection with the embodiments described in FIG. 1 for example, the projections 202 may be present along with a cutter tool 112.

Figure 3A:
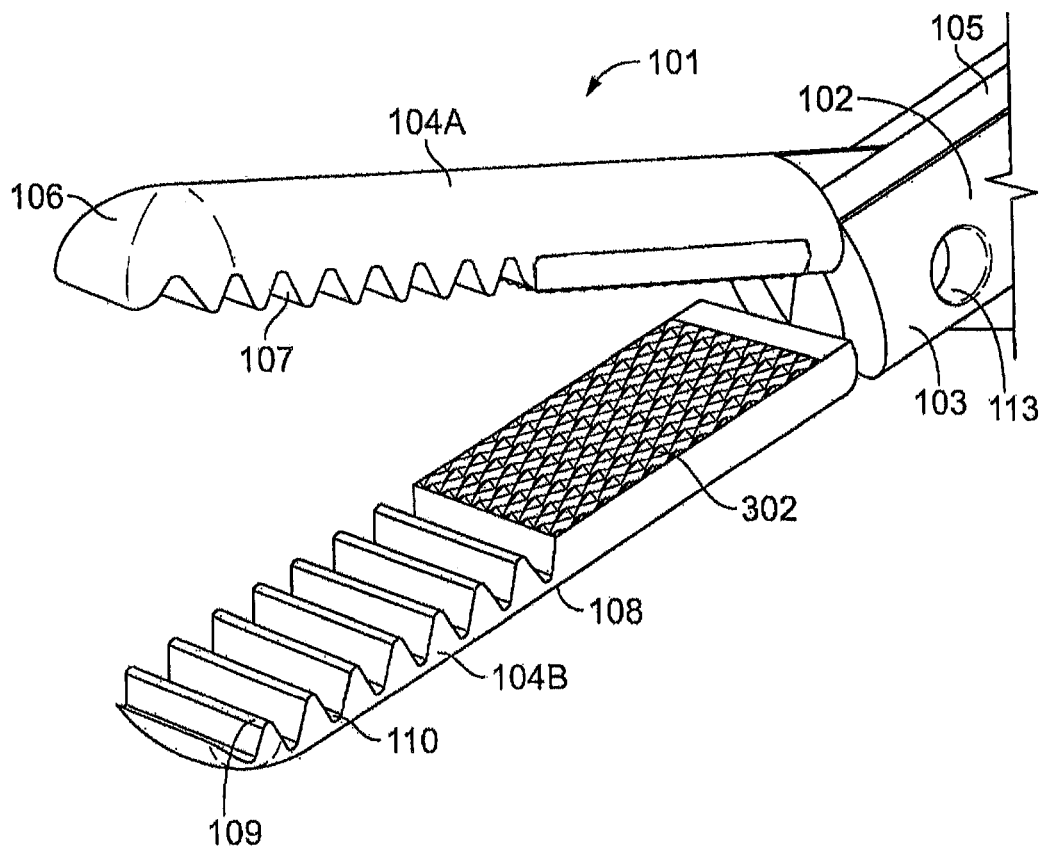
FIGS. 3A-3B illustrate a tissue grasper in an open configuration, according to further embodiments of the present disclosure.
Figure 3B:
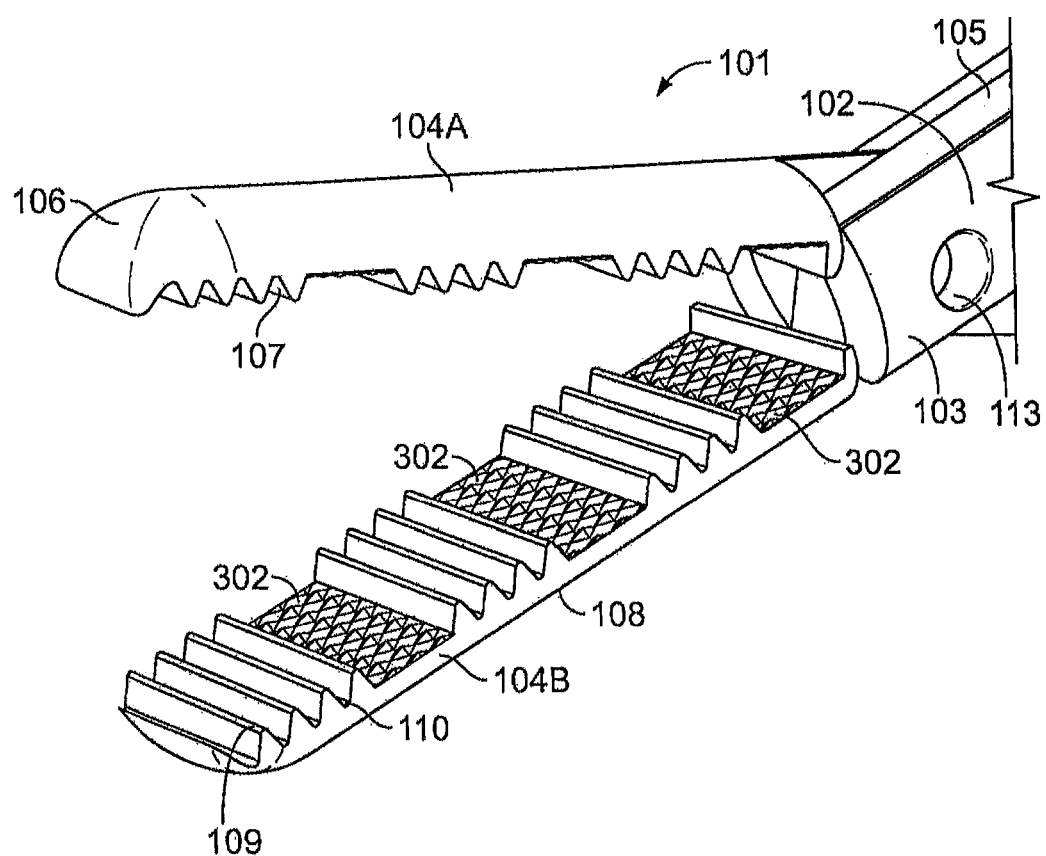

FIG. 3A depicts a tissue grasper 100 according to another embodiment of the present disclosure. The inner surface 107, as shown in FIG. 3, includes ridges 109 and grooves 110, as explained in the previous embodiments. The inner surface 107 may also be partially ridged. The ridges 109 may be present at a proximal or distal region, or alternatively may be present on both the proximal and distal regions of the distal end 106 of the arm 104, and there may be a patch of region along the inner surface 107 that is free from any ridges 109 ("unridged portion 302") as shown in FIG. 3B. The unridged portion 302 may include a non-slippery surface, which in turn may have a roughened surface to increase friction. The multiple teeth and/or surface configurations could be used for, as an example, grasping different tissue types, including, but not limited to, thick and dense tissue, thick and soft tissue, and thin and light tissue. In addition, grasping other surgical devices such as needles or sutures.

The unridged portion 302 as shown FIGS. 3A-B may be used as an anvil to strike, for example, a staple, a fastener, or a clip, through the grasped tissue. Staples may be disposed on the inner surface 107 of the upper arm 104A. When the arms 104 move towards each other the staples may be forced into the tissue. The unridged portion 302 provides a surface where the free ends of the staples fold upon themselves to securely attach to the tissue. Similar mechanisms may also be implemented in the embodiment as described by FIGS. 1A-1D, where as the cutting element 112 slices through the tissue the cut ends of the tissue may be stapled simultaneously to prevent bleeding. The staples may be present on the axis parallel to the channel 111 such that the staples do not interfere with the movement of the cutting element 112.

A needle (not shown) may be disposed at the unridged portion 302 of this embodiment, and the end-effector 101 used as a needle holder for suturing. The unridged portion 302 may also be further used to hold the suture during a surgical maneuver. The surface may also include an adhesive coating, depressions, or slots to accommodate a needle. The surface may also be made of materials such as fabric, plastic, rubber, ceramic, or metal. The present embodiment may further be used along with the previous embodiments.

Figure 4:
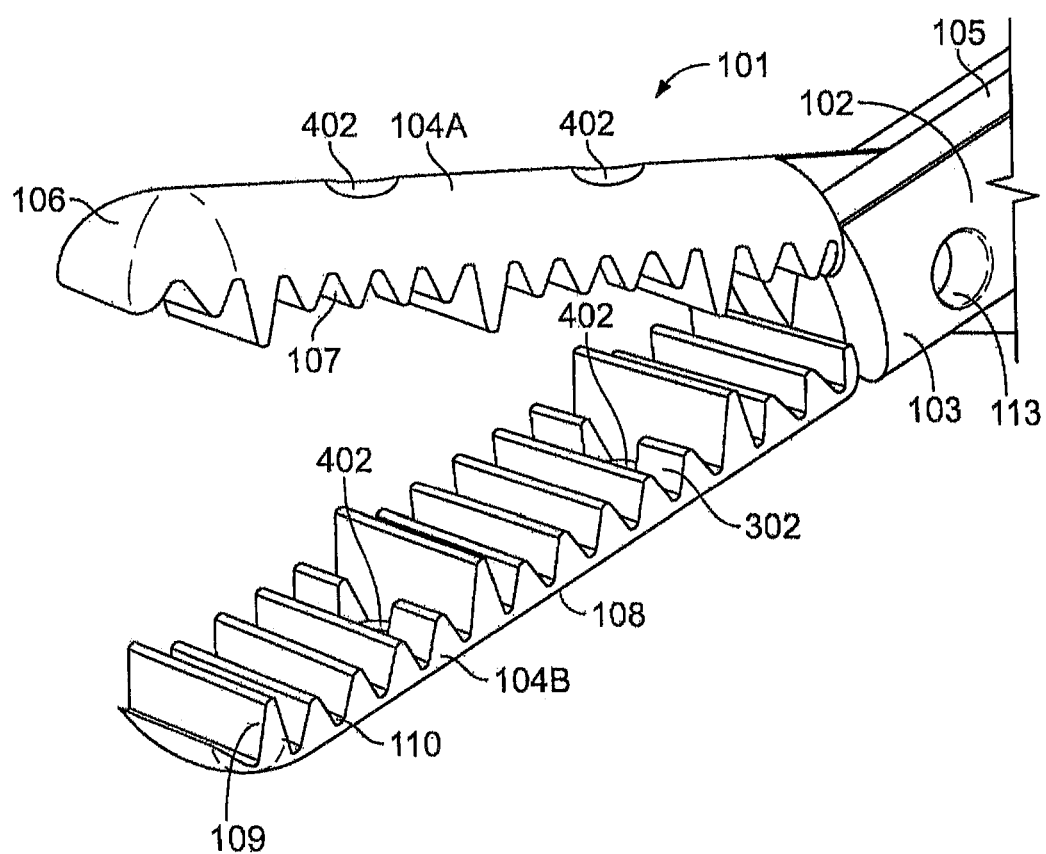
FIG. 4 illustrates a tissue grasper in an open configuration, according to another embodiment of the present disclosure.

The ridges 109 as shown in the FIGS. 1-3 may not be uniform in shape and dimension. For example, as shown in FIG. 4, some of the ridges 109 may be larger than the others. The slope of the ridges 109 may be different for each ridge. The ridges 109 may have a plateau on the top surface as shown in the FIGS. 1-3. Alternatively, the ridges 109 may have a sharp or blunt surface based on the texture and properties of the tissue to be handled. Ridges of various shapes, sizes, and orientations may coexist on the same inner surface 107.

The arms 104 may include holes 402 on their inner surface 107, which extends to the outer surface 108. The holes 402 form a passage through which fluids from the tissues may be squeezed out. The holes 402 on one arm may also line up with holes 402 on the opposite arm thereby a though hole may be formed. Needles, pins, fasteners or any instrument of suitable dimensions may be inserted through the holes 402. In some embodiments, arms 104 may be hollow having a channel that is connected to a vacuum pump to assist in holding tissue.

Further, the arms 104 may also include a locking mechanism to fix them in a specific position. Grasped tissue may be held indefinitely without application of force to the control member by locking the arms 104 in position. Locking means may include any suitable mechanism, such as snap fit, screw, or fastening means. The arms 104 may also include a magnetic element and may be locked by the magnetic attraction.

In alternate embodiments, the inner surface 107 may be detachable. The arms 104 may include locking mechanisms to which the inner surface 107 may be attached. Alternatively, the arms 104 may also be detachable from the elongate member 102.

The outer surface 108 of the arms 104 may comprise an atraumatic surface with beveled edges as shown in the various embodiments of this disclosure. Alternatively, the outer surface 108 may also include abrasive elements, barbed projections, or tissue retracting arms. Additional modifications such as abrasive elements provide further tissue manipulating capabilities such as scraping removing unwanted tissue growth, plaques, and deposits. Barbed projections on the outer surface 108 may attach to the tissues and may be used to remove debris and sectioned tissues from narrow vessels. In some embodiments, notches may be cut into arms to assist in tissue grasping when arms 104 are pushed or pulled through tissue. The dimensions of the notches may vary, as desired. In addition, various alternatives of the notches may be contemplated without departing from the scope of the present disclosure. Retracting arms may prevent interference from surrounding tissue and may aid the physician in manipulating sequestered tissues.

Other embodiments of the present disclosure will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. A medical instrument comprising:
a member having a proximal end and a distal end;
an end effector having a first arm and a second arm, wherein the first arm and the second arm are coupled to the distal end of the member, and the first arm and the second arm are moveable relative to one another;
a first plurality of ridges and a second plurality of ridges, wherein the first plurality of ridges and the second plurality of ridges extend along the first arm
a first unridged portion on the first arm, facing the second arm, proximal to the first plurality of ridges of the first arm, and distal to the second plurality of ridges of the first arm, wherein the first unridged portion extends along an entire lateral width of the first arm, wherein a lateral direction is perpendicular to a longitudinal axis of the first arm, and wherein the longitudinal axis extends from a proximal end of the first arm to a distal end of the first arm;
a second unridged portion on the first arm, facing the second arm, proximal to the second plurality of ridges, wherein the second unridged portion extends along the entire lateral width of the first arm; and
a third plurality of ridges, wherein the third plurality of ridges extend along the first arm, wherein axes extending along apexes of the third plurality of ridges of the first arm intersect one another.

2. The medical instrument of claim 1, further comprising: one or more staples positioned along at least a portion of the second arm, opposite the first unridged portion of the first arm or the second unridged portion of the first arm, wherein the first unridged portion of the first arm or the second unridged portion of the first arm includes an anvil for striking the one or more staples.

3. The medical instrument of claim 1, wherein at least one of the first arm or the second arm defines an aperture, extending through a thickness of at least one of the first arm or the second arm.

4. The medical instrument of claim 3, wherein the aperture is a first aperture, wherein the first arm defines the first aperture extending through a thickness of the first arm, and wherein the second arm defines a second aperture extending through a thickness of the second arm.

5. The medical instrument of claim 4, wherein the first aperture is longitudinally aligned with the second aperture.

6. The medical instrument of claim 1, wherein at least some of the first plurality of ridges of the first arm and at least some of the second plurality of ridges of the first arm extend along the entire lateral width of the first arm.

7. The medical instrument of claim 1, wherein the second arm comprises:
a fourth plurality of ridges;
a fifth plurality of ridges;
a third unridged portion, facing the first arm, proximal to the fourth plurality of ridges, and distal to the fifth plurality of ridges, wherein the third unridged portion extends along an entire lateral width of the second arm, wherein a lateral direction is perpendicular to a longitudinal axis of the second arm, and wherein the longitudinal axis extends from a proximal end of the second arm to a distal end of the second arm; and
a fourth unridged portion, facing the first arm, proximal to the fifth plurality of ridges, wherein the fourth unridged portion extends along the entire lateral width of the second arm.

8. The medical instrument of claim 1, wherein each ridge of the first plurality of ridges defines an apex and a trough, wherein a height of the apex is greater than a height of the trough, wherein a height direction extends perpendicularly to the longitudinal axis of the first arm and perpendicularly to the lateral direction, and wherein a height of the trough of each ridge of the first plurality of ridges is the same as a height of the first unridged portion;
wherein each ridge of the second plurality of ridges defines an apex and a trough, wherein a height of the apex is greater than a height of the trough, and wherein a height of the trough of each ridge of the second plurality of ridges is the same as a height of the second unridged portion.

* * * * *